United States Patent [19]

Rutenberg et al.

[11] Patent Number: 5,655,029

[45] Date of Patent: Aug. 5, 1997

[54] DEVICE AND METHOD FOR FACILITATING INSPECTION OF A SPECIMEN

[75] Inventors: Mark R. Rutenberg, Monsey; Robert Tjon-Fo-Sang, Valley Cottage; Leonid Strinkovsky, Spring Valley; Laurie J. Mango, Roosevelt Island; James C. Herriman, Huntington Station, all of N.Y.

[73] Assignee: Neuromedical Systems, Inc., Suffern, N.Y.

[21] Appl. No.: 741,297

[22] Filed: Oct. 30, 1996

Related U.S. Application Data

[63] Continuation of Ser. No. 280,293, Jul. 26, 1994, abandoned, which is a continuation-in-part of Ser. No. 944,819, Sep. 14, 1992, Pat. No. 5,333,207, which is a continuation of Ser. No. 610,423, Nov. 7, 1990, abandoned.

[51] Int. Cl.$^6$ .................................................. G06K 9/03
[52] U.S. Cl. ........................................ 382/133; 382/311
[58] Field of Search ........................... 382/100, 128, 382/133, 134, 291, 311, 318, 319; 356/39; 364/413.08, 413.1

[56] References Cited

U.S. PATENT DOCUMENTS

| | | | |
|---|---|---|---|
| 4,404,683 | 9/1983 | Kobayashi et al. | 382/6 |
| 4,464,652 | 8/1984 | Lapson et al. | 340/710 |
| 4,513,438 | 4/1985 | Graham et al. | 382/6 |
| 4,587,520 | 5/1986 | Astle | 340/712 |
| 4,592,089 | 5/1986 | Hartman | 382/6 |
| 4,672,683 | 6/1987 | Matsueda | 382/57 |
| 4,812,909 | 3/1989 | Yokobayashi et al. | 358/183 |
| 4,862,390 | 8/1989 | Weiner | 364/521 |
| 4,931,783 | 6/1990 | Atkinson | 340/710 |
| 4,952,051 | 8/1990 | Lovell et al. | 352/87 |
| 4,965,725 | 10/1990 | Rutenberg | 364/413.1 |
| 5,068,906 | 11/1991 | Kosaka | 382/48 |
| 5,073,857 | 12/1991 | Peters et al. | 364/413.1 |
| 5,257,182 | 10/1993 | Luck et al. | 364/413.1 |
| 5,287,272 | 2/1994 | Rutenberg et al. | 364/413.01 |
| 5,333,207 | 7/1994 | Rutenberg | 382/6 |

OTHER PUBLICATIONS

"A Quantum Leap in Quantitative Analysis", Becton Dickinson, The CAS Workstation, Quantitative Proliferation Index, brochure (No Date).

"New PAPNET Cytological Screening System," Oct. 1989 Neuromedical Systems, Inc. (brochure).

*Primary Examiner*—Andrew Johns
*Attorney, Agent, or Firm*—Renner, Otto, Boisselle & Sklar

[57] ABSTRACT

A device for the visual inspection of a specimen, comprising a first microscope for obtaining a magnified view of different areas of a specimen, a display monitor for displaying images of at least a subset of the different areas of the specimen, selection means for enabling the selection of a image displayed on the monitor, a second microscope for review of an area of the specimen corresponding to the selected image, a motorized stage for positioning said specimen with respect to the field of view of the second microscope, and a processor for determining the image selected and instructing the motorized stage to position the specimen so that the area of the specimen corresponding to the selected image is in the field of view of the second microscope.

10 Claims, 3 Drawing Sheets

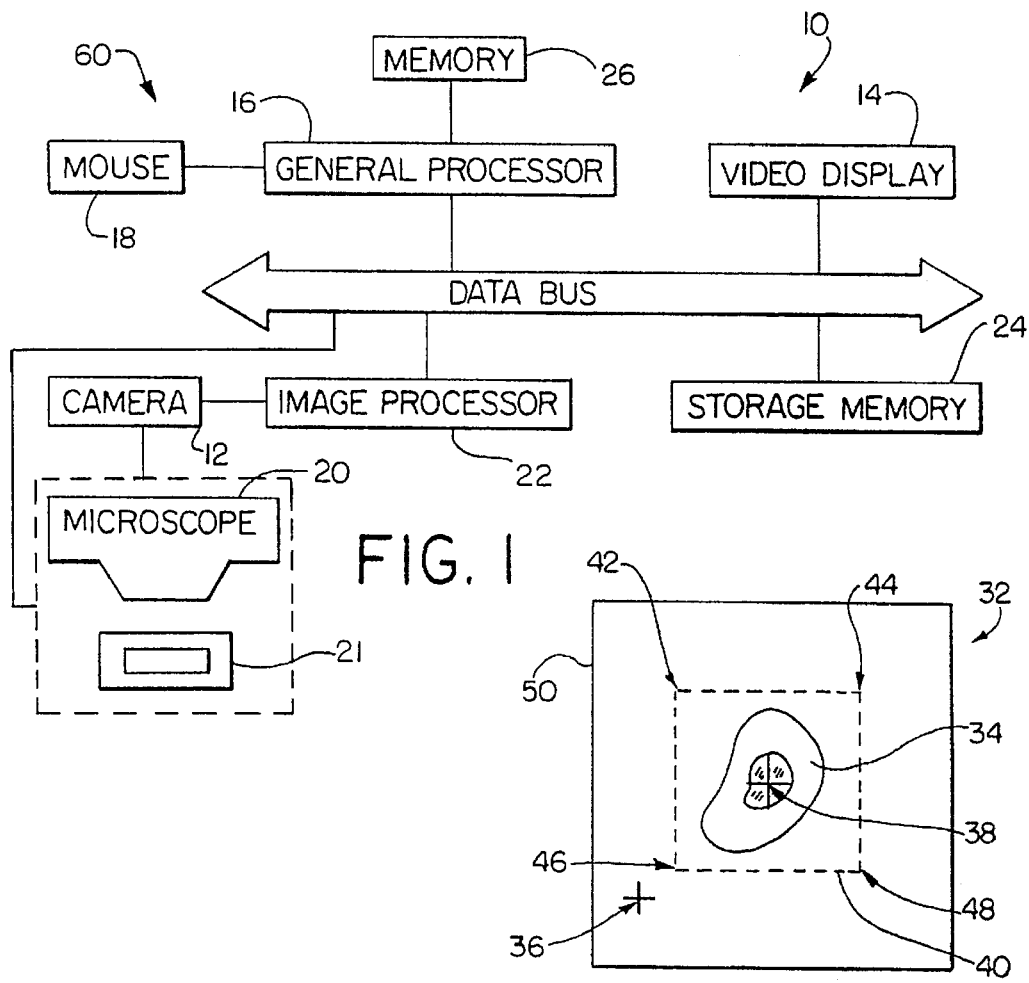
FIG. 1
FIG. 3
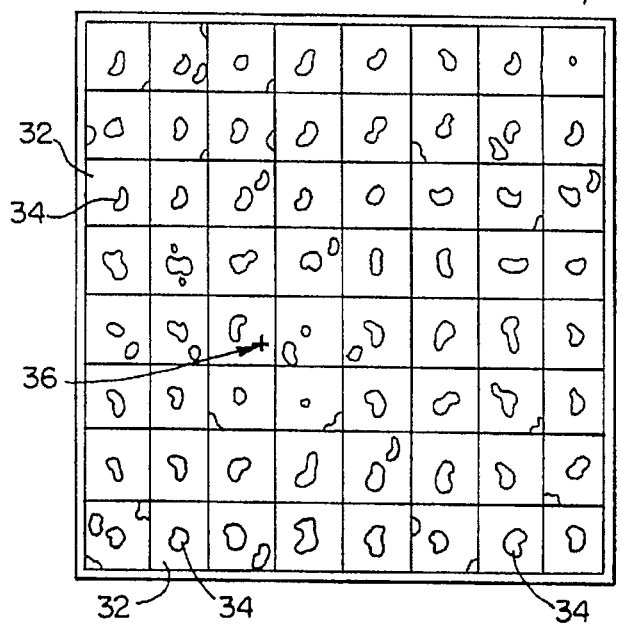
FIG. 2

DEVICE AND METHOD FOR FACILITATING INSPECTION OF A SPECIMEN

This is a continuation of application Ser. No. 08/280,293 filed on Jul. 26, 1994, now abandoned, which is a continuation-in-part of U.S. patent application Ser. No. 07/944,819, filed Sep. 14, 1992, which issued on Jul. 26, 1994, as U.S. Pat. No. 5,333,207, and U.S. patent application Ser. No. 07/610,423 filed Nov. 7, 1990, now abandoned both entitled, "Inspection Apparatus And Method With Inspection Auditing For Images Presented On A Display."

FIELD OF THE INVENTION

The present invention relates to an apparatus and method for the visual inspection of an image, and, more particularly, to a device and method for facilitating the review of a selected specimen or area of interest with a microscope.

BACKGROUND OF THE INVENTION

Often objects requiring an inspection cannot be inspected by the naked eye. Consequently, the inspection process must be accomplished by viewing an image of the object, such as an image displayed on a high resolution video monitor. This may be necessary when the object to be inspected is very small and requires magnification to be properly inspected or when the object is located in a hazardous or otherwise inaccessible environment.

A couple of examples of such a situation is the inspection of cellular matter on a slide for the presence of malignant or premalignant cells, as in a Pap smear screening process, and the inspection of semiconductor chips. In these instances a number of objects or a single object having a number of areas of interest, are displayed on a video screen. An inspection technologist or inspection technician then inspects the individual objects or areas for flaws, defects, or certain criteria indicative of an event or condition. Many inspection processes require a skilled technician to review hundreds or thousands of images per day for the detection of only a few flaws or occurrences. These inspection procedures can become quite tedious, tending to detract from the overall quality of the inspection performed by even the most conscientious of technicians. Further, the non-detection of a certain condition, such as the presence of a single malignant cell among thousands of benign cells, can have very severe adverse consequences. While the display of the image of the object facilitates inspection, it does little to ensure that the inspection is adequate.

It would be desirable to provide a method or a device which controls or audits the inspection process of a displayed image of the object in such a way as to increase the probability of an adequate inspection.

SUMMARY OF THE INVENTION

The present invention provides a device and method for automatically repositioning an area of a specimen in the field of view of a microscope to facilitate a technician directly viewing an area of the specimen which was found to be significant in a review of a number of images of different areas of the specimen. The device includes a display upon which a number of images are presented and a mouse, for example, which allows the technician to select an image on the display for view through a microscope.

In accordance with one aspect of the present invention, a device for the visual inspection of a specimen includes a first microscope for obtaining a magnified view of different areas of a specimen, a display monitor for displaying images of at least a subset of the different areas of the specimen, a selector for enabling the selection of a image displayed on the monitor, a second microscope for obtaining a view of an area of the specimen corresponding to the selected image, a motorized stage for positioning the specimen with respect to the field of view of the second microscope, and a processor for determining the image selected and instructing the motorized stage to position the specimen so that the area of the specimen corresponding to the selected image is in the field of view of the second microscope.

In accordance with another aspect of the invention, a device for the visual inspection of a specimen includes a storage memory for storing images and locations of different areas of a specimen, a display monitor for displaying at least a subset of the stored images, a selector for enabling the selection of a image displayed on the monitor, a microscope for obtaining a magnified view of the specimen, a motorized stage for positioning the specimen with respect to the field of view of the microscope, and a processor for determining the image selected and instructing the motorized stage to position the specimen in accordance with the stored location of the area on the specimen corresponding to said selected image.

In accordance with a further aspect of the invention, a method for facilitating the inspection of a specimen includes the steps of positioning a specimen in the field of view of a microscope to obtain views of different parts of a specimen, displaying images of the views, detecting the selection by an operator of at least one of the images, and repositioning the specimen so that the selected image is in the field of view of a microscope.

These and other objects, advantages, features and aspects of the present invention will become apparent as the following description proceeds.

To the accomplishments of the foregoing and related ends, the invention, then comprises the features hereinafter fully described in the specification and particularly pointed out in claims, the following description and the annexed drawings setting forth in detail a certain illustrative embodiment of the invention, this being indicative, however, of but one of the various ways in which the principals of the invention may be employed. It will be appreciated that the scope of the invention is to be determined by the claims and the equivalents thereof.

BRIEF DESCRIPTION OF THE DRAWINGS

In the annexed drawings:

FIG. 1 is a schematic illustration of a viewing and inspection auditing device in accordance with the present invention;

FIG. 2 is an illustration of an exemplary inspection display screen;

FIG. 3 is a close-up view of a portion of the display screen of FIG. 2;

DETAILED DESCRIPTION OF THE INVENTION

Figure 4:
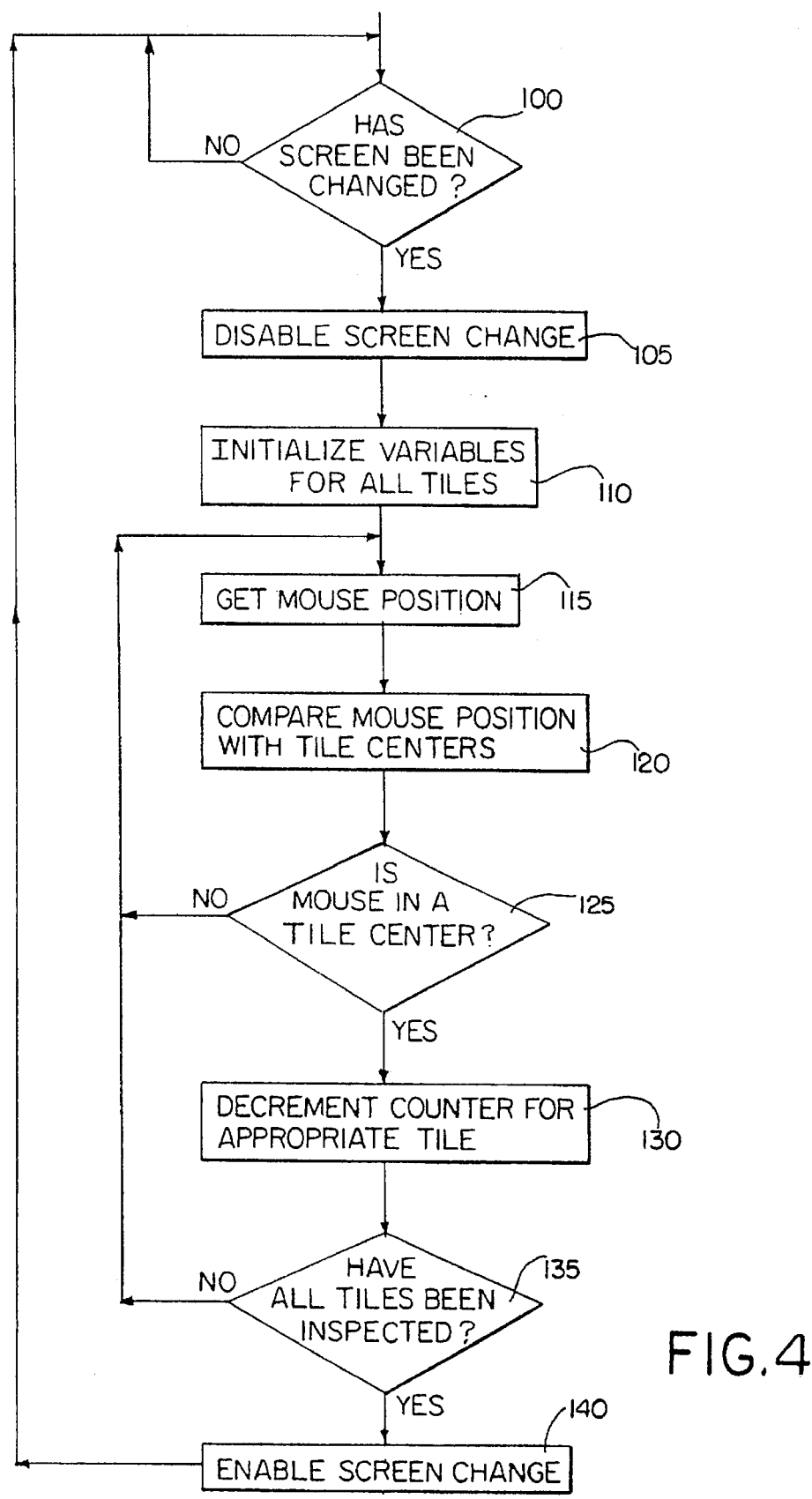
FIGS. 4 is a flowchart of an inspection auditing algorithm in accordance with the present invention.

With reference now to the several figures in which like reference numerals depict like items, and initially to FIG. 1 there is shown an exemplary inspection apparatus 10 employing the features of the present invention. The apparatus 10 includes a camera 12 for capturing an image of an object, a monitor 14 for displaying the captured image for inspection purposes, and a general processor 16 and mouse 18 for facilitating the auditing features of the invention. The apparatus 10 may include a microscope 20 to magnify small or microscopic objects to a size suitable for inspection and display on the monitor 14. The microscope 20 would thus have particular use when the object to be inspected is a cell or group of cells. Preferably, the microscope 20 is automated in that it is associated with a motorized stage 21 which is capable of presenting different areas of an object or specimen within the field of view of the microscope as determined by the general processor 16. The motorized stage 21 may be a part of the microscope 20 or may be a separate element functioning in concert with the microscope. An optional image processor 22 may also be included to perform various image processing functions, such as automated inspection and/or classifying functions, on the image captured by the camera 12 prior to display on the monitor 14.

To facilitate discussion of the present invention the following description will focus on an exemplary automated Pap smear screening process. It will be appreciated however that the invention is not limited to the auditing of a Pap smear screening process, but has broad application in any visual inspection process carried out by a person on a displayed image of an object.

In the exemplary embodiment the objects to be inspected are a number of cells contained among, for example, 200,000 cells in a Pap smear specimen disposed on a slide. The inspection apparatus is tailored to accommodate locating and displaying relatively few microscopic cells of the many cells of the specimen. The displayed cells would be those, for example, which appear most likely to be malignant or premalignant. Such an automated Pap smear screening system is marketed by Neuromedical Systems, Inc., of Suffern, New York under the trademark PAPNET®. The PAPNET® screening system and related screening systems and methods are further disclosed in U.S. Pat. Nos. 4,965,725 and 5,287,272 and in U.S. patent application Ser. Nos. 07/425,665, 07/502,611, 08/196,714 and 08/196,982 all of which are incorporated by this reference.

Preferably the inspection and auditing apparatus 10 is automated to at least some degree. The microscope 20 is preferably automated and is capable of scanning the specimen while the camera 12 grabs an image of the view provided by the microscope. The image is then digitized and preferably provided to the image processor 22.

The image processor 22 may be equipped to perform its own automated inspection of the imaged objects in addition to the inspection of the displayed images performed by the inspection technician. Preferably, the image processor 22 also includes functions directed to determining specific locations of interest in an object, such as the centroid of a cell, to aid in the auditing functions of the invention.

In the exemplary embodiment of the invention, the image processor 22 performs a morphological filtering of the image received from the camera 12 to determine a number of objects in the image which are of the same approximate size as a malignant or premalignant cervical cell. A secondary classification is also performed by a neural network to further reduce the number of images which must be inspected by a cytotechnician. The resultant images and their corresponding coordinates in the specimen are then transferred to the general processor 16 for storage in the memory 24 and for display by the monitor 14.

It has been found that the screening functions performed by the primary and secondary classifiers in series will, for a specimen having at least one premalignant or malignant cell, rank at least one premalignant or malignant cell among the highest 64 ranked cells in the specimen. For this reason it is generally sufficient that the cytotechnician closely examines only the 64 highest ranked cells. It has further been found that it is deskable that the 64 highest ranked cell images, or tiles, be presented in an 8×8 matrix 30 of tiles 32, as is shown in FIG. 2 or in some other sequence, arrangement, etc., for example, four screens of a 4×4 matrix of tiles. Consequently, the cytotechnician will individually examine each of the sixty-four displayed cellular images 34 centered in a tile 32, and identify any possibly malignant images for storage in memory 24 and later analysis by a pathologist. A representative tile is illustrated in FIG. 3 with a cell centered within the tile. The cytotechnician will then command the device to display the next screen of sixty-four images, and an inspection of these images will be performed.

The commands to the general processor 16 to store the image of a possibly malignant cell (e.g., for subsequent review by a pathologist), the commands to display the next screen of images, and other commands to the processor 16 may be accomplished through entering the appropriate sequence of keystrokes in the keyboard or through the use of a conventional mouse-driven cursor. The mouse 18 may be a mechanical mouse or optical mouse. In the case of a mouse activated system, the cytotechnician may move a cursor appearing on the display to the area of the possibly malignant image and depress a key on the mouse 18 which would command the general processor 16 to store that image in the memory 24. Alternatively, the system may employ a mouse driven menu configuration, such as is known in the art, to command the general processor 16 to perform a certain function, or the mouse could be equipped with multiple keys for the selection of separate functions. The use of mouses is well known in the art and there are several commercially available mouses and software drivers to operate the mouse for a number of different computer manufacturers. Variations on the manner in which the cytotechnician (inspection technician) interfaces with the general processor 16 will be apparent to those of ordinary skill in the art and are within the scope of the invention. Other manners in which the technician can interface with the general processor 16 include a light pen, a track ball and a keyboard, for example.

While most cytotechnicians attempt to individually inspect each cell in a specimen, the economic pressures on a cytotechnician to examine an increasing number of slides a day are tremendous. While United States federal regulation of the Pap smear inspection process mandates that a cytotechnician inspect only a prescribed number, for example, eighty, specimen slides per day to maintain quality of inspection and/or to minimize fatigue, this is no guarantee that each possibly malignant cell will be adequately inspected.

The present invention, however, provides a means requiring the cytotechnician to direct his or her attention and focus to each and every cellular image on the display to alleviate this problem. Using the mouse 18, the cytotechnician must drag the display cursor 36 to within a certain tolerance of the approximate center 38 of each image 34 of the sixty-four tiles 32 that are presented and maintain the mouse in that respective center for a period of time sufficient for a cytotechnician to perform an adequate classification of the imaged cell. In the cytological classifier embodiment of the invention a view of primarily only a single cell is approximately centered in the image area (also referred to as tile herein). The position information of the cursor, such as its X and Y coordinates, is transferred to the general processor 16 such as through a port, which is conventional. If the positional information matches, to within a certain tolerance, the center of the image, then the general processor 16 notes that the image has been examined. The indication that the image has been examined, as evidenced from the cursor 36 being approximately centered on an image 34 for a sufficient period of time to perform an adequate inspection, may be indicated on the display 30 such as by highlighting the perimeter of the tile 32 or by some other means.

Recalling that there are a number of discrete images on the display, preferably an 8×8 matrix 30 of sixty-four tiles 32, with the suspect cell 34 pre-centered in each image, the cytotechnician must devote at least a substantial amount of attention to the suspect cell in order to correctly center the cursor 36 in each tile in order to move to the next screen or specimen slide. Only after the cursor 36 has been approximately centered on each image 34 on the screen 30 for a sufficient period of time will the general processor 16 allow the next set of images 30 to be displayed on the monitor 14. The display of the next set of images 30 may be automatic or may be the result of the cytotechnician manipulating the cursor 36 to a set location on the screen and clicking the mouse 18 or through a certain sequence of keystrokes.

Referring to FIG. 4, there is shown a relatively detailed flowchart illustrating the step-by-step functions preferably performed to accomplish the features described above. In the discussion below reference numerals contained with parentheses designate like numbered steps in the flowchart of FIG. 4. After a screen 30 consisting of, preferably, sixty-four tiles 32 has been displayed on the monitor 14, the mouse routine 95 will begin determining whether the cursor 36 has appeared within a certain number of pixels of a tile center 38 for a sufficient duration of time for a cytotechnician to perform an adequate inspection of the image 34 centered in that tile. Initially, the routine 95 will determine whether the screen 30 has recently been changed to display a new set of sixty-four images (100). If not, meaning that a new screen 30 has not been requested by the cytotechnician since all the tiles 32 of the last screen have been inspected, the routine 95 will not perform any cursor checking. If the screen 30 has been changed, then further screen changing is disabled (105), thus preventing a new screen from being displayed by the general processor 16, regardless of whether such a change is requested by the cytotechnician. A separate decremental timer is then initialized for each of the sixty-four tiles 32 in the screen 30 (110). These decremental timers are set at a number sufficiently high that number multiplied by the time period between obtaining cursor 36 positions from the port will equal a time which has been determined to be sufficiently long in duration for a cytotechnician to adequately inspect a tile 32 to determine whether the image 34 centered in that tile should be tagged for further analysis by a cytologist. The X and Y coordinates of the screen cursor 36 as determined by the mouse 18 are then obtained from a port, as is conventional (115). Note that while this port is continually refreshed with the current position of the screen cursor 36, the routine will access that port and obtain the X and Y coordinates of the screen cursor only once every certain duration as determined by a timing circuit in the general processor 16 or the time it takes to execute a pass through the routine 95.

The decremental timers (counters) may be set to a count of one in which case the simple passing of the mouse controlled screen cursor through the appropriate place in a tile for a time that is long enough to be detected there will be an acceptable time.

After the coordinates of the screen cursor 36 have been obtained, the X and Y coordinates are compared against predetermined values to determine whether the cursor 36 lies within a certain distance of the tile center 38 (120). If the maximum tolerance distance is held constant at all positions around the tile center 38, a circle is formed within which the screen cursor 36 must lie in order for the corresponding decremental timer to be decremented. However, as this is somewhat computationally intensive, preferably the coordinates of the screen cursor 36 are checked to determine whether they lie within a square or tolerance box 40 formed around the tile center. This facilitates determining whether the cursor is within a certain boxed tolerance of the centerpoint. Consequently, to define the tolerance box 40 surrounding the center 38 of each tile 32, only four values need be predetermined and stored, for example, the X coordinate at the top left corner 42 of the box, the Y coordinate at the top right corner 44 of the box, the Y coordinate at the bottom left corner 46 of the box, and finally the X coordinate at the bottom right corner of 48 the box. By comparing whether the X coordinate of the screen cursor 36 lies between the top left X coordinate and the bottom right corner X coordinate, and whether the Y coordinate of the screen cursor is between the top right corner Y coordinate and bottom left corner Y coordinate, it can be determined whether the screen cursor lies within this tolerance box 40 (125).

If the cursor 36 is not within the tolerance box 40 surrounding a tile center 38, then no further action is taken until the next cursor position is obtained from the port. If the cursor 36 lies within the tolerance box 40 centered around a tile center 38, the decremental counter for that tile 32 is decremented by one (130). It is then determined whether the decremental counter for each of the sixty-four tiles 32 has been decremented to zero (135). If not, then no further action in the routine 95 is taken until the timed period has elapsed to obtain a new cursor position from the port. If, however, the decremental timer for all tiles 32 have been decremented to zero, then the screen change is enabled (140). Consequently, when the cytotechnician requests that the screen 30 be updated to display a new set of sixty-four images, the general processor 16 will acknowledge the request and display the next screen 30 of images 34. When the routine 95 now checks to determine whether the screen 30 has been changed (100) it will determine that it has, and the ability to change the screen to display a new set of sixty-four images will be disabled until those images have been inspected (105).

It is noted that the flowchart of FIG. 4 illustrates only those functions related to the cursor checking routine. The general processor 16 will, of course, perform other functions in between the time periods in which the cursor 36 position is obtained, and that position is checked to determine whether it lies within the tolerance box 40 of a tile center 38. Also note that, if the cytotechnician has determined that a certain tile 32 merits further review by a cytologist, that tile is stored for future review, and the decremental timer for that tile is immediately set to zero, as if that tile had been inspected for the appropriate duration of time.

Each time the decremental timer for a certain tile 32 has been decremented to zero an indication will be made on the screen that tile has been examined for an acceptable duration of time. Such an indication may be through highlighting the perimeter 50 of the tile 32, or making some other visual notation within that tile.

In the preferred embodiment, it is not necessary that the cytotechnician manipulate the screen cursor 36, via the mouse 18, to the center 38 of a tile 32 and leave it there for the complete time duration. It is only necessary that the screen cursor 36 appear within the tolerance box 40 around a tile center 38 and that the routine 95 confirms the presence of the cursor within the tolerance box a certain number of times. Consequently, the cytotechnician may compare two different tiles 32 on the screen 30, and move the screen cursor to the approximate center 38 of each tile back and forth a couple times if he or she so desires. It is only necessary that the composite time that the screen cursor 36 spends within the tolerance box 40 is sufficient to indicate an adequate inspection of that tile.

While the above routine refers to an embodiment wherein tiles may be inspected simultaneously, it would be obvious to one of ordinary skill in the art that the routine could be simply modified to require that each tile be inspected separately for a set period of time before moving the cursor to the next tile, or that the timing functions could be removed altogether requiring only that the routine confirms that the screen cursor 36 has been moved through the tolerance box 40 surrounding each tile center 38. This latter embodiment without the timing constraints would have particular application when a person performing the inspection would recognize a flaw or that a cell was malignant very quickly, or as quickly as he or she could position the cursor near the center 38 of a tile 32 and the routine 95 could confirm that the cursor has been moved within the required tolerance of the tile center.

Given the description above and a reasonable amount of time and effort, one of ordinary skill in the art of programming microcomputers could write the software code in the appropriate language following the flow chart of FIG. 4 to interface with the mouse and an internal or external timing circuit to reduce the features above into a format suitable for execution by the general processor. The resultant code would then be loaded into memory 26 accessible by the general processor 16. It would also be apparent to one of skill in the art that equivalent devices, such as a light pen, for example, could be substituted for the mouse, with corresponding changes to the interface hardware and the software drivers, to accomplish the same results as the mouse.

In some instances it may be desirable that the technician review not only the images presented on the display 14, but that the technician review through a microscope actual views of an object or specimen that has been identified on the display as being of concern. This may be the case when reviewing and classifying a Pap smear for the presence of malignant cells. In such a review and classification it is often beneficial for the technician to view not only a cell in isolation, but also to view the contextual surround of the cell, i.e., the material on the slide in the vicinity of the suspect cell. The surrounding material can confirm to the technician whether the suspect cell is malignant or benign or whether the cell is part of an overall grouping of cells, in which case the technician may also be able to diagnose certain malignancy types. Further, a microscope view is often better in color, contrast and in resolution than a recreation of the image on a display.

Review of the actual view of the object or cell is facilitated by employing a microscope system 20 having a motorized stage 21, as shown in FIG. 1, with the motorized stage being in communication with the general processor 16. The motorized stage 21 positions an area of a specimen or slide mounted thereon with respect to the field of view of microscope 20 based on information, such as X and Y coordinates, received from the general processor 16. An exemplary microscope is manufactured by Carl Zeiss, Inc. of Germany, and a suitable motorized stage is manufactured by Ludl Electric Products, Ltd. of Hawthorne, N.Y.

When a technician detects on the display 14 a cell image which is suspected of being a malignant cell, the technician selects the cell image for review through the microscope 20 such as by positioning a screen cursor on the cell image and depressing a button on a mouse, for example. The selection of the cell image is transferred to the general processor 16 which in turn sends appropriate coordinate information, such as X and Y coordinates of the center of the image, to the motorized stage 21. The motorized stage 21 thus repositions the area of the slide or specimen mounted thereon which corresponds to the selected image in the field of view of the microscope 20. When the technician then views the specimen through the microscope 20, the technician will see the area of the specimen containing the suspect cell, preferably with the suspect cell centered in the field of view. The technician may also scan the area and surrounding areas with the microscope 20 using the motorized stage 21 to affect the repositioning of the specimen with relation to the field of view of the microscope.

Figure 5:
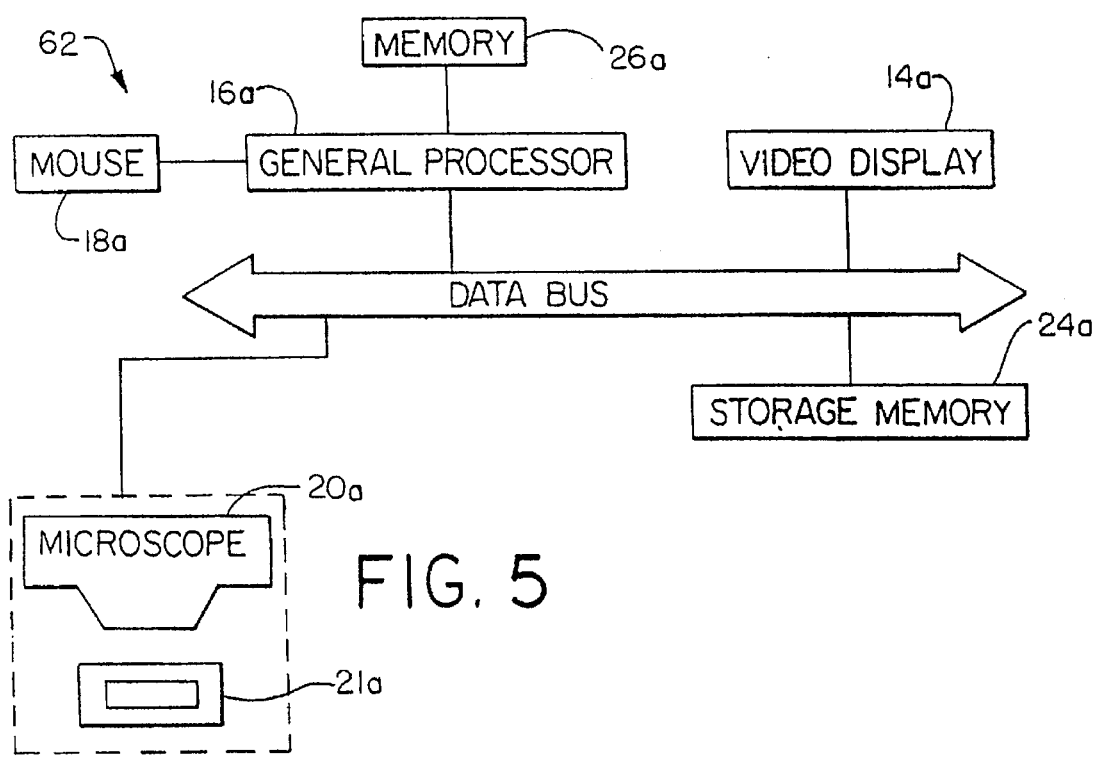
FIG. 5 is a schematic illustration of a review station.

In some applications it is advantageous for the scanning of the specimen and the review of the scanned images to take place at separate stations. In such an instance the scanning station 60, which scans a specimen and stores images for later review by a technician, would be substantially as shown in FIG. 1, although the video display 14 may not be necessary if no review of images were to take place at the scanning station. A separate review station 62 for the review of previously scanned images is shown in FIG. 5. The review station 62, like the scanning station, preferably includes a general processor 16a with memory 26a and a mouse 18a, a storage memory 24a for storing images to be reviewed, a video display 14a for the display of the stored images, a microscope 20a and a motorized stage 21a. The review station 62 need not include a dedicated image processor or a camera since the images have already been created and possibly partially classified by the scanning station 60. In this embodiment, the scanned specimen is taken from the scanning station 60 along with the stored images and their coordinate locations on the specimen, which may be stored on electronic media or an optical disk, for instance, to a review station 62. The specimen is then placed on the motorized stage 21a and the images are loaded into storage memory 24a. The technician then calls up the images on the display 14a and reviews the images as discussed above. If the technician detects an image on the display 14a which is suspicious, the image is selected, such as by positioning a screen cursor on the image and depressing a certain button on a mouse 18a. The general processor 16a then determines the coordinates of the area of the specimen corresponding to the selected image and transfers the coordinate information to the motorized stage 21a which positions the appropriate area of the specimen in the field of view of the microscope 20a. The technician can then examine the actual magnified view of the suspicious cell or other object as well as the contextual surround through the microscope 20a.

It will be appreciated that while the example depicted is that of inspecting cells that are suspected to be malignant or premalignant, the routine could be applied to any inspection technique. For example, the routine could be used to determine whether a computerized inspection of a microchip was being performed adequately, or for any other computerized application, such as the inspection of the image of a human heart, or a simple mechanical gear. Additionally, while in the described example the location to which the technician's interest was being directed was the center of the image, the routine could be applied to a location other than the center of the image or to several locations within the image.

While it is still possible to circumvent the inspection checks of the invention, a skilled cytotechnician would have to practically intentionally ignore the morphology of the cellular images being displayed to avoid performing at least a cursory inspection of the images.

What is claimed is:

1. A system for the visual inspection of a specimen, comprising:

a scanning device including a microscope for obtaining images of magnified views of different areas of a specimen; and a reviewing device located at a location remote from the location of the scanning device for reviewing images obtained by the scanning device; the reviewing device including:

a display monitor for displaying at least a subset of said images;

a selection means for enabling the selection of one of the images displayed on said monitor that is to be viewed through a microscope concurrently with the image being displayed on the display monitor;

a second microscope for obtaining a view of an area of the specimen corresponding to the selected image;

a motorized stage for positioning said specimen with respect to the field of view of said second microscope; and a processor for determining the image selected and instructing said motorized stage to position said specimen so that the area of the specimen corresponding to said selected image is in the field of view of said second microscope.

2. The system of claim 1, said selection means including a mouse.

3. The system of claim 1, said selection means including a light pen.

4. The system of claim 1, said selection means including a track ball.

5. The system of claim 1, said selection means including a keyboard.

6. The system of claim 1, said scanning device further including a processor for classifying images in said specimen.

7. The system of claim 1, wherein said specimen is a biological specimen.

8. The system of claim 1, wherein said specimen is a cytological specimen.

9. The system of claim 1, wherein said specimen is a histological specimen.

10. The system of claim 1, wherein said specimen is affixed to a slide.

* * * * *